(12) United States Patent
Govari

(10) Patent No.: US 9,425,860 B2
(45) Date of Patent: Aug. 23, 2016

(54) TWO WIRE SIGNAL TRANSMISSION

(71) Applicant: BIOSENSE WEBSTER (ISRAEL), LTD., Yokneam (IL)

(72) Inventor: Assaf Govari, Haifa (IL)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 615 days.

(21) Appl. No.: 13/946,031

(22) Filed: Jul. 19, 2013

(65) Prior Publication Data

US 2015/0023374 A1   Jan. 22, 2015

(51) Int. Cl.
*H04B 3/60* (2006.01)
*A61B 5/06* (2006.01)
*A61B 5/00* (2006.01)

(52) U.S. Cl.
CPC *H04B 3/60* (2013.01); *A61B 5/062* (2013.01); *A61B 5/6852* (2013.01); *A61B 2562/222* (2013.01); *H04Q 2213/13106* (2013.01); *H04Q 2213/13305* (2013.01)

(58) Field of Classification Search
None
See application file for complete search history.

(56) References Cited

U.S. PATENT DOCUMENTS

| 6,304,769 | B1 | 10/2001 | Arenson et al. | |
| 8,357,152 | B2 | 1/2013 | Govari et al. | |
| 8,945,095 | B2 * | 2/2015 | Blumenkranz | A61B 19/46 606/1 |
| 2005/0018201 | A1 * | 1/2005 | de Boer | A61B 5/0059 356/479 |
| 2006/0244973 | A1 * | 11/2006 | Yun | A61B 5/0059 356/511 |
| 2008/0205551 | A1 | 8/2008 | Lo et al. | |
| 2009/0299174 | A1 | 12/2009 | Wright et al. | |
| 2012/0123509 | A1 * | 5/2012 | Merrill | A61F 7/0085 607/105 |
| 2013/0122824 | A1 | 5/2013 | Schell | |
| 2013/0154867 | A1 | 6/2013 | Dosho et al. | |

OTHER PUBLICATIONS

European Search report for corresponding Application No. EP14177839 dated Jan. 9, 2015.

* cited by examiner

*Primary Examiner* — Christine Duong

(57) ABSTRACT

Apparatus, including a first signal source generating a first signal and a second signal source generating a second signal. A cross-over switch is connected between the two sources so as to generate in a direct switch configuration a sum of the first and second signals and in a crossed switch configuration a difference between the first and second signals. The apparatus includes a processor which is configured to receive the sum and the difference, and to recover the first signal and the second signal therefrom.

20 Claims, 5 Drawing Sheets

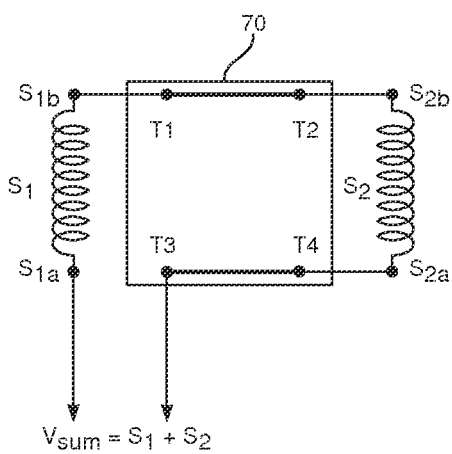
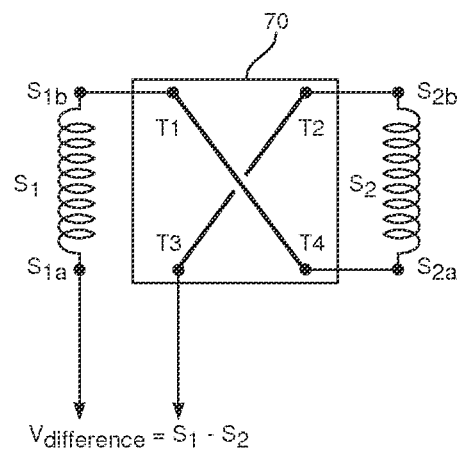
FIG. 3A
FIG. 3B

TWO WIRE SIGNAL TRANSMISSION

FIELD OF THE INVENTION

The present invention relates generally to signal transmission using conductors, and specifically to transmitting multiple signals over a minimal number of conductors.

BACKGROUND OF THE INVENTION

In many fields, a relatively large number of measurements may need to be made simultaneously, and the measurements may need to be transferred from the place of measurement to a distant location. Such transference may be difficult because of limited access between the place of measurement and the distant location. In minimally invasive medical surgery for example, the size of the access to a patient undergoing the surgery may be extremely limited, so that catheters or tools used for the surgery need to have diameters of the order of millimeters. Minimizing the number of conductors used to transfer the measurements enables the diameters of the catheters or tools to be reduced, with corresponding benefit to the patient.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides apparatus, including:

a first signal source generating a first signal and a second signal source generating a second signal;

a cross-over switch connected between the two sources so as to generate in a direct switch configuration a sum of the first and second signals and in a crossed switch configuration a difference between the first and second signals; and a processor configured to receive the sum and the difference, and to recover the first signal and the second signal therefrom.

In a disclosed embodiment the apparatus includes a pair of conductors, respectively connected to the first signal source and to the cross-over switch, which are configured to convey therefrom the sum and the difference to the processor.

In a further disclosed embodiment the first and the second signals consist of analog signals.

In a yet further disclosed embodiment the apparatus includes a distal end of a catheter, configured for insertion into a human patient, wherein the first signal source, the second signal source, and the cross-over switch are incorporated. Typically, the first and the second signal sources respectively include first and second coils configured to generate respectively the first signal and the second signal in response to magnetic fields generated external to the distal end, and the processor is configured to determine an indication of a location and an orientation of the distal end in response to the first signal and The second signal.

In an alternative embodiment the processor is configured to toggle the cross-over switch between the direct switch configuration and the crossed switch configuration.

There is further provided, according to an embodiment of the present invention, apparatus, including:

a sequence of n signal sources respectively generating n signals, where n is an integer greater than one;

(n−1) cross-over switches, each cross-over switch being connected between a $p^{th}$ signal source and a $(p+1)^{th}$ signal source, where p is an integer and $1 \leq p < n$, the (n−1) cross-over switches being configured to generate n different linear combinations of the n signals; and a processor configured receive the linear combinations, and to recover the n signals therefrom.

Typically, the processor is configured to cycle the (n−1) cross-over switches through n configurations of the switches so as to respectively generate the n different linear combinations of the n signals.

Respective coefficients of the n signals in the different linear combinations may be +1 or −1.

The apparatus may include a pair of conductors, respectively connected to a first of the n signal sources and to an $(n-1)^{th}$ cross-over switch, which are configured to convey the linear combinations to the processor.

There is further provided, according to an embodiment of the present invention a method, including:

generating a first signal from a first signal source and generating a second signal from a second signal source;

connecting a cross-over switch between the two sources so as to generate in a direct switch configuration a sum of the first and second signals and in a crossed switch configuration a difference between the first and second signals;

receiving the sum and the difference;

and recovering the first signal and the second signal from the sum and difference.

The method may include providing a distal end of a catheter configured for insertion into a human patient, and incorporating the first signal source, the second signal source, and the cross-over switch into the distal end.

There is further provided, according an embodiment of the present invention, a method, including:

respectively generating n signals from a sequence of n signal sources, where n is an integer greater than one;

connecting each of (n−1) cross-over switches between a $p^{th}$ signal source and a $(p+1)^{th}$ signal source, where p is an integer and $1 \leq p < n$, the (n−1) cross-over switches being configured to generate n different linear combinations of the n signals;

receiving the linear combinations; and recovering the n signals from the received linear combinations.

The present disclosure will be more fully understood from the following detailed description of the embodiments thereof, taken together with the drawings, in which:

BRIEF DESCRIPTION OF THE DRAWINGS

FIG. 3A and FIG. 3B are schematic circuit, diagrams illustrating a cross-over switch, according to an embodiment of the present invention;

DETAILED DESCRIPTION OF EMBODIMENTS

Overview

Figure 1:
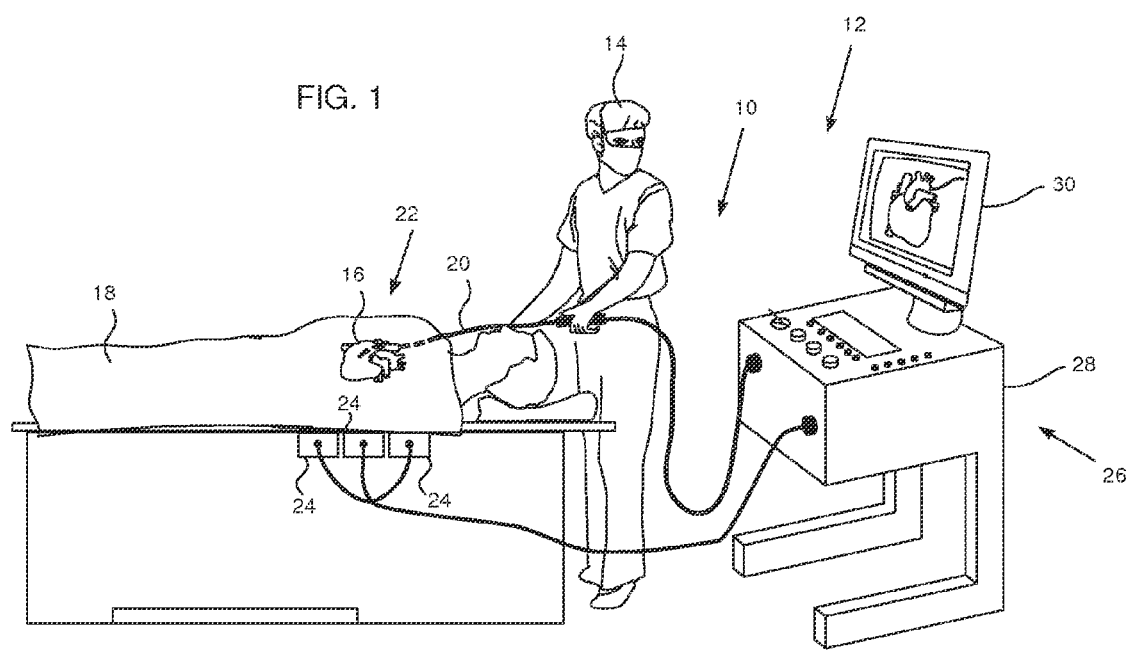
FIG. 1 is a schematic illustration of an invasive medical procedure using a two wire transmission system, according to an embodiment of the present invention.

An embodiment of the present invention provides a method for transferring multiple signals, typically analog signals, using a minimal number of conductors. Typically, only a single pair of conductors are required to transfer the multiple signals.

In the case where the multiple signals comprise two signals from two signal sources, a cross-over switch having two configurations is connected between the two sources. In a "direct" configuration the switch generates a sum of the first and second signals; and in a "crossed" configuration the switch generates a difference between the first and second signals. The sum and the difference are conveyed to a processor, typically via the single pair of conductors referred to above, and the processor recovers the two signals by analysis of the received sum and difference.

In the case where the multiple signals comprise more than two signals from a corresponding number of signal sources, more cross--over switches are used. In general, for n signal sources (n a positive integer) (n−1) cross-over switches are connected between the n sources. Typically, the configuration of the switches is altered in sequence, so that at any one time no more than one of the switches is in the crossed configuration, providing a "local" difference between the two signals connected to the switch. For each configuration of the switches a different linear combination of the signals is generated, each linear combination comprising a signal sum with at most one signal difference.

The different linear combinations may be conveyed to the processor via a single pair of conductors, and the processor may recover each of the n signals by analysis of the linear combinations.

Embodiments of the present invention enable multiple signals to be sampled substantially simultaneously, and the signals may be transferred for subsequent recovery by a processor using a single pair of conductors. Once recovered, the processor has all of the signals available at all times, in contrast to a time multiplexing system of signal transfer, where the signals are available sequentially.

System Description

In the following description, like elements in the drawings are identified by like numerals, and the like elements are differentiated as necessary by appending a letter to the identifying numeral.

Figure 2:
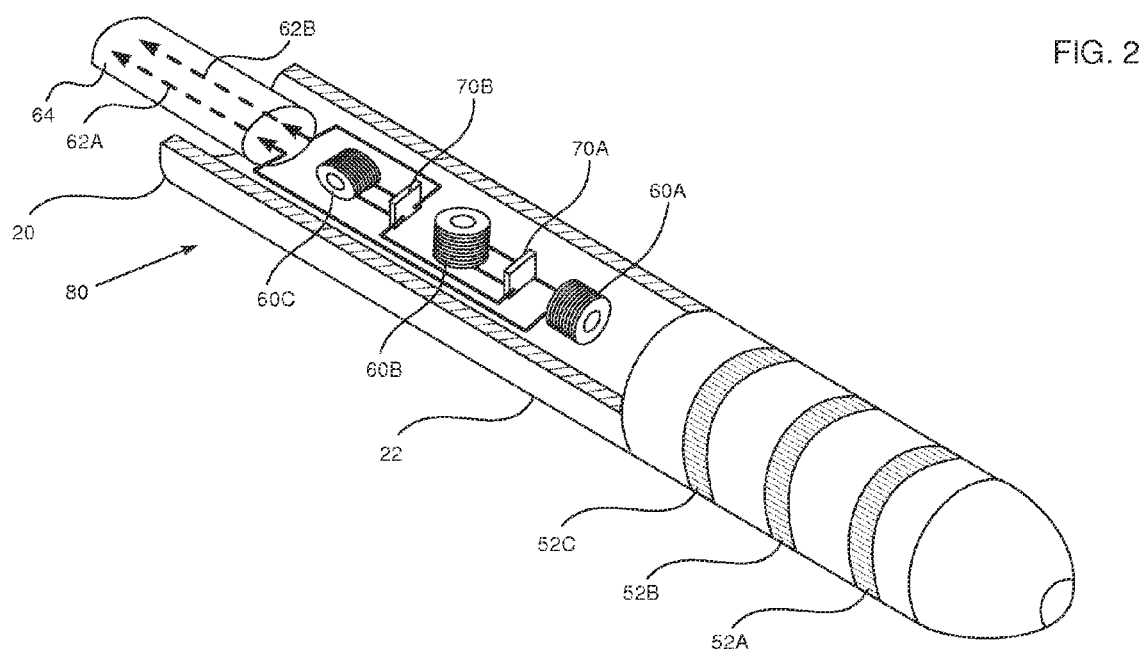
FIG. 2 is a schematic illustration of a distal end of a catheter used in the procedure, according to an embodiment of the present invention.

FIG. 1 is a schematic illustration of an invasive medical procedure using a two wire transmission system 10, and FIG. 2 is a schematic illustration of a distal end of a catheter used in the procedure, according to embodiments of the present invention. By way of example, system 10 is assumed to be incorporated into an apparatus 12 used for an invasive medical procedure, performed by a medical professional 14, on a heart 16 of a human patient 18.

To perform the procedure, professional 11 inserts a catheter 20 into the patient, so that a distal end 22 of the catheter enters the heart of the patient. In order to track the distal end while it is in the patient's heart, apparatus 12 comprises magnetic transmitters 24, typically located beneath and external to the patient, in the vicinity of heart 16. Transmitters 24 are powered and controlled by a processor 26, which is located in an operating console 28 of apparatus 12. The Carto® system produced by Biosense Webster, of Diamond Bar, Calif., uses such a tracking method.

As explained in more detail below, signals generated within distal end 22, in response to the magnetic fields from the transmitters, are transferred back via catheter 20 to processor 26. The processor analyzes the received signals to determine a location and an orientation of the distal end, and may present the results on a screen 30 attached to the console. The results are typically presented by incorporating an icon representing the distal end into a map of the heart.

Other signals generated within the distal end, examples of which are provided, below, may also be transferred back via catheter 20, and results from analysis of the signals may be presented on screen 30. The results derived from these signals typically include numerical, displays, and/or graphs representative of characteristics of the heart.

FIG. 2 schematically shows elements of distal end 22. The distal end typically comprises one or more sensing elements used to measure characteristics of the part of heart 16 wherein distal end 22 is located. Such sensing elements may comprise, for example, a sensor measuring a force or pressure applied by the distal end to the heart, a sensor measuring a temperature of the heart, and/or an electrode measuring an electropotential of the heart. For example, U.S. Pat. No. 8,357,152 to Govari, et al., whose disclosure is incorporated herein by reference, describes a system having a sensor generating pressure-sensing signals in the distal end of a catheter. As will be apparent from the following description, signals provided by the type of sensors described above may be conveyed to processor 26 in embodiments of the present invention.

By way of example, distal end 22 is assumed to comprise three generally similar electrodes 50, electrodes 52A, 52B, and 52C, which may be used to measure heart electropotentials. In some embodiments electrodes 52A, 52B, and/or 52C may also be used to apply radio-frequency ablation power to the heart.

For the measurements from the sensing elements, such as electrodes 50, to be useful, it is typically necessary to know a location and orientation of the distal end wherein the elements are located. In order to provide the location and orientation, the distal end comprises three generally similar coils 60, coils 60A, 60B, and 60C, which are arranged, to have axes that are mutually perpendicular to each other. For clarity the figure shows the coils as having separated centers; however, the coils may be configured to have a common center in order to save space. The coils generate the signals that are received by processor 26 (and referred to above) in response to the magnetic fields from transmitters 24. However, rather than each signal being transferred back to the processor via a respective pair of conductors for each coil 60, in embodiments of the present invention the three coil signals are transferred back to processor 26 via a single pair of conductors 62, conductors 62A, 62B, as explained below. Conductors 62 are typically enclosed in a cable 64 which is incorporated into catheter 20.

In order to transfer the signals by pair of conductors 62, coils 60 are connected to two cross-over switches 70, switches 70A and 70B. Characteristics of cross-over switches 70, used in embodiments of the present invention, are explained below. The arrangement of coils 60, switches 70, and conductors 62 in the distal end is herein termed circuit 80.

FIG. 3A and FIG. 3D are schematic circuit diagrams respectively illustrating a first "direct" configuration of a generic cross-over switch 70, and a second "crossed-over" configuration of the switch, according to an embodiment of the present invention. Switch 70 may be in one of the two configurations, the characteristics of which are described below. Switch 70 comprises four isolated terminals T1, T2, T3, and T4. In the first configuration terminals T1 and T2 are connected together, and terminals T3 and T4 are connected together. In the second configuration terminals T1 and T4 are connected together, and terminals T3 and T2 are connected together.

Switch is connected to two signal sources, typically analog signal sources, respectively generating signals $S_1$ and $S_2$. In general, expressions for $S_1$ and $S_2$ are given by equation (1)

$$S_1 = A_1 e^{i\omega_1 \phi_1}; \quad S_2 = A_2 e^{i\omega_2 \phi_2} \tag{1}$$

where $A_1$, $A_2$ are amplitudes, $\omega_1$, $\omega_2$ are frequencies, and $\phi_1$, $\phi_1$ are phases of the signals.

The signal sources generating signals $S_1$ and $S_2$ are illustrated by way of example in FIGS. 3A and 3B as coils. While the sources may in fact be coils, there is no requirement that this is the case, and the entities generating signals $S_1$ and $S_2$ may be any elements or combination of elements that give signals that may be represented by equation (1).

Signal $S_1$ is developed between source terminals $S_{1a}$ and $S_{1b}$; similarly, signal. $S_2$ is developed between source terminals $S_{2a}$ and $S_{2b}$. The sources are connected to switch 70 as shown in the figures, i.e., source terminal. $S_{1b}$ is connected to switch terminal T1, source terminals $S_{2a}$ and $S_{2b}$ are respectively connected to switch terminals T2 and T4; and an output from the switched sources is taken between source terminal $S_{1a}$ and switch terminal T3.

In the first, direct, configuration of switch 70, an output $V_{sum}$ between terminals $S_{1a}$ and T3 is a sum of the two signals, i.e., $$V_{sum} = S_1 + S_2 \tag{2}$$

In the second, crossed, configuration of switch 70, an output $V_{difference}$ between terminals $S_{1a}$ and T3 is a sum of the first signal with a reversed polarity of the second signal, corresponding to a difference of the two signals, i.e., $$V_{difference} = S_1 + (-S_2) = S_1 - S_2 \tag{3}$$

In embodiments of the present invention, cross-over switches 70 may be implemented by any suitable process known in the art. Such processes include, but are not limited to, producing switches as the microelectromechanical systems (MEMS) or as application specific integrated circuits (ASICs). The configuration of each switch 70, i.e., if a specific switch 70 is in its first direct configuration or in its second crossed configuration, is under control of processor 26 which is able to toggle the switch between the two configurations. For simplicity control links to the switches from the processor, enabling the toggling, are not shown in the diagram.

Figure 4A:
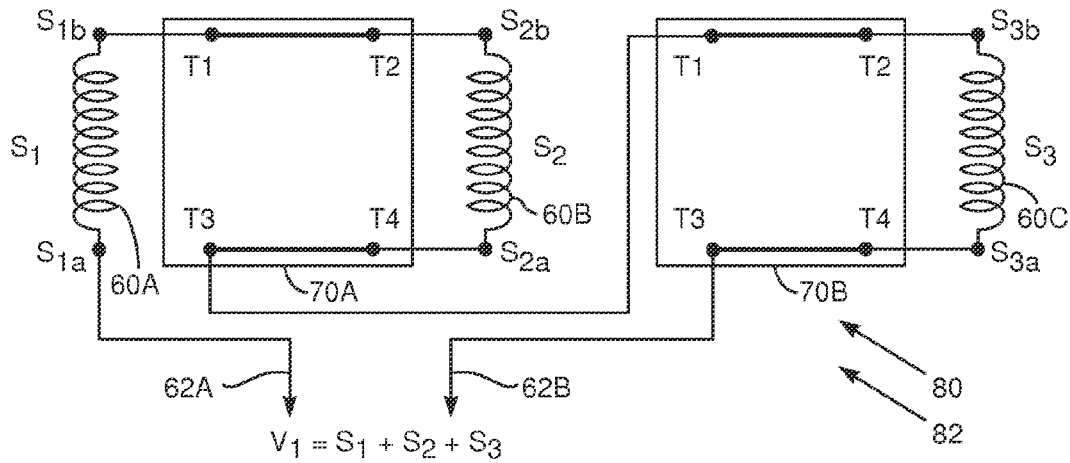
FIGS. 4A, 4B, and 4C are schematic circuit diagrams of different configurations of a circuit in the distal end of the catheter of FIG. 2, according to an embodiment of the present invention.
Figure 4B:
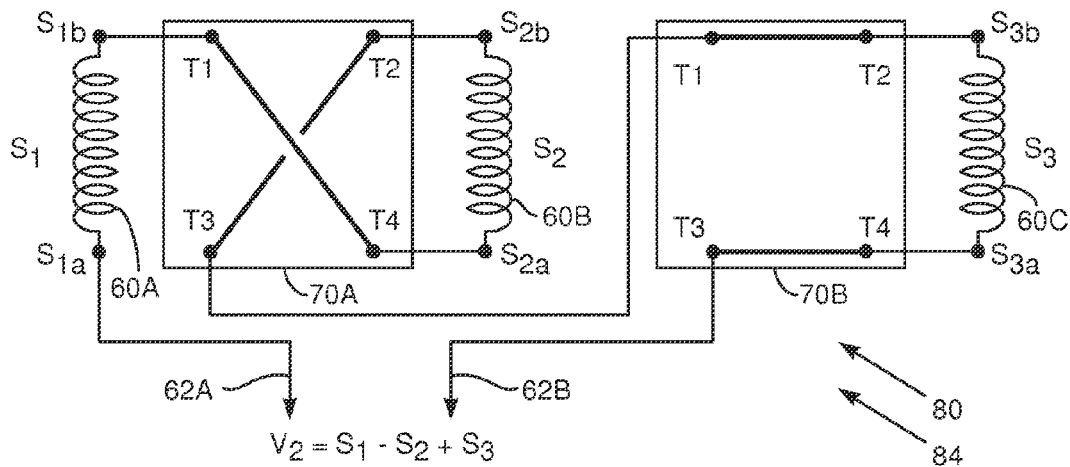
Figure 4C:
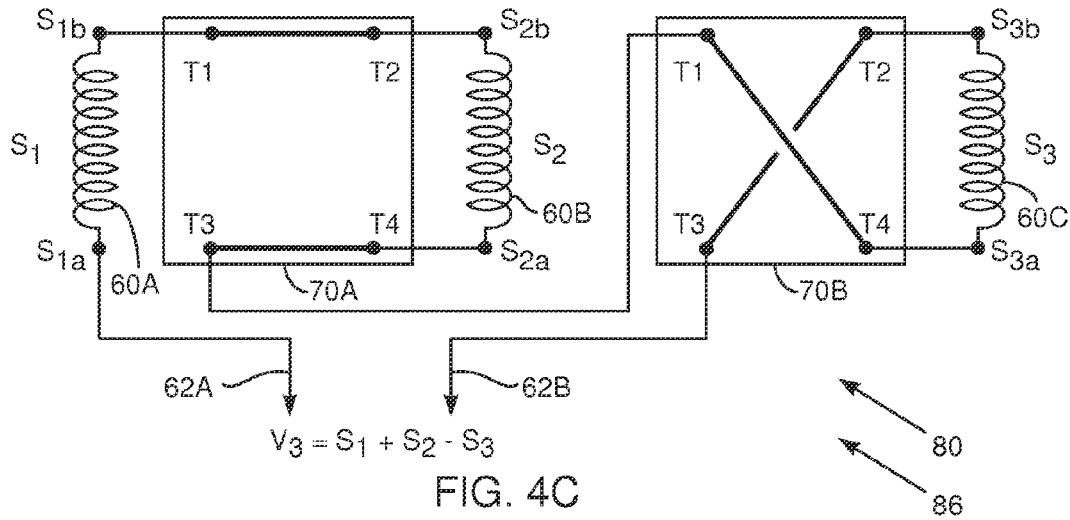

FIGS. 4A, 4B, and 4C are schematic circuit diagrams of different configurations of circuit 80 in distal end 22, according to an embodiment of the present invention. As stated above, cross-over switches 70A and 70B are connected to coils 60C, 60B, and 60A, and the connections are as shown in FIGS. 4A, 4B, and 4C. To illustrate the equivalence of switch 70B with generic switch 70 (shown in FIGS. 3A and 3B) switch 70A is shown connected to coils 60A and 60B which have also been respectively labeled as sources generating signals $S_1$ and $S_2$. As in FIGS. 3A and 3B the sources have terminals $S_{1a}$, $S_{1b}$, $S_{2a}$ and $S_{2b}$.

Switch 70B is also equivalent to generic switch 70 having a source corresponding to coil 60C and generating a signal $S_3$ connected to the switch. Coil 60C has source terminals $S_{3a}$, $S_{3b}$ which are respectively connected to switch 70B terminals T4, T2.

However, in the circuits of FIGS. 4A, 4B, and 4C terminal T3 of switch 70A is connected to switch 70B terminal T1, and an output from the circuits is taken between source terminal $S_{1a}$ and switch 70B terminal T3, which are respectively connected to conductors 62A and 62B.

In an embodiment of the present invention processor reconfigures circuit 80 in a cyclic manner, setting the configuration of the circuit as shown in FIG. 4A, then in FIG. 4B, then in FIG. 4C, and returning to the configuration of FIG. 4A. The periodicity of the cyclic reconfiguration is typically dependent on the characteristics of signals $S_1$, $S_2$, and $S_3$. $S_1$ and $S_2$ are assumed to be of the form described above by equation (1); signal $S_3$ is assumed to be of a similar character, and to have an equation of the form:

$$S_3 = A_3 e^{i\omega_3 \phi_3} \tag{4}$$

where $A_3$ is an amplitude, $\omega_3$ is a frequency, and $\phi_3$ is a phase of signal $S_3$.

For example, if the frequencies $\omega_1$, $\omega_2$, $\omega_3$ of the signals are of the order of 10 kHz, then processor 26 may set a frequency of switching between the different configurations of circuit 80 to be of the order of 1 kHz, so that a different configuration occurs approximately each millisecond. Other suitable frequencies of switching between the configurations will be apparent to those having ordinary skill in the art, and all such frequencies are assumed to be within the scope of the present invention.

FIG. 4A illustrates a first configuration 82 of circuit 80, wherein switches 70A and 70B are both in the direct configuration. In this case an output from conductors 62 is:

$$V_1 = S_1 + S_2 + S_3 \tag{5}$$

FIG. 4B illustrates a second configuration 84 of circuit 80, wherein switch 70B is in the direct configuration and switch 70A is in the crossed configuration. In this case an output from conductors 62 is:

$$V_2 = S_1 - S_2 + S_3 \tag{6}$$

FIG. 4C illustrates a third configuration 86 of circuit 80, wherein switch 70B is in the crossed configuration and switch 70A is in the direct configuration. In this case an output from conductors 62 is:

$$V_3 = S_1 + S_2 - S_3 \tag{7}$$

While switching between the three configurations of circuit 80 described above, processor 26 receives values of $V_1$, $V_2$, and $V_3$. By inspection of equations (5), (6), and (7), the following expressions for $S_1$, $S_2$, and $S_3$ may be derived:

$$S_1 = \frac{V_2 + V_3}{2} \tag{8}$$

$$S_2 = \frac{V_1 - V_2}{2} \tag{9}$$

$$S_3 = \frac{V_1 - V_3}{2} \tag{10}$$

Processor 26 may apply, equations (8), (9), and (10), or a method equivalent to application of the equations, in order to derive values of $S_1$, $S_2$, and $S_3$ from measured values $V_1$, $V_2$, and $V_3$.

The examples described above with reference to FIGS. 2, 3A, 3B, 4A, 4B, and 4C illustrate circuits having one cross-over switch with two signal sources connected to the switch, and two cross-over switches with three signal sources connected to the switches. However, these are particular examples, and embodiments of the present invention include circuits having n signal sources, with (n−1) cross-over switches connected between the sources, where n is any integer greater than one.

Figure 5:
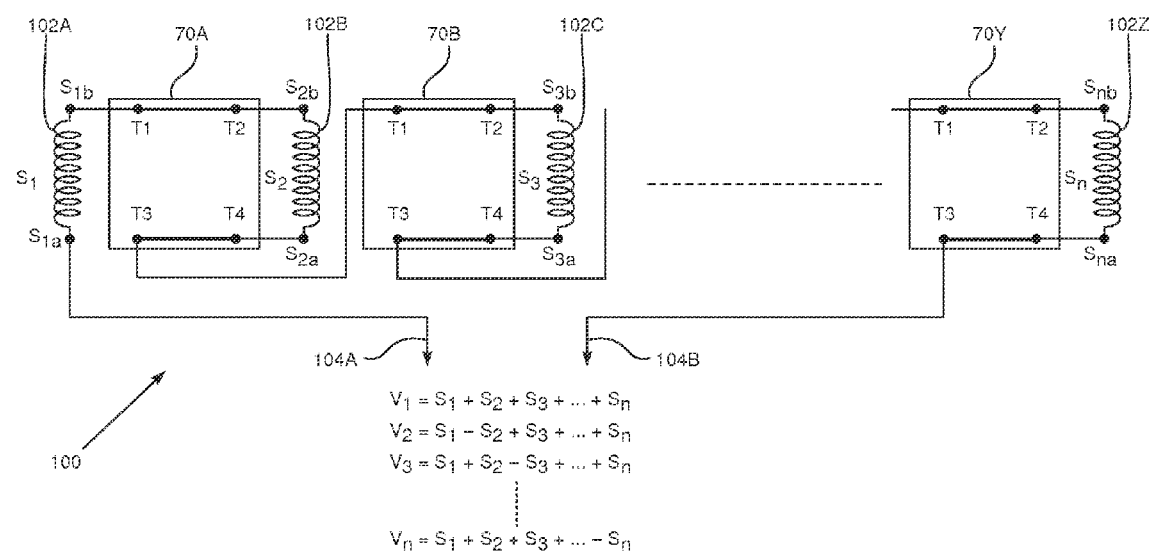
FIG. 5 is a schematic circuit diagram of a sequence of multiple signal sources connected by cross-over switches, according to an embodiment of the present invention.

FIG. 5 is a schematic circuit diagram of a sequence of multiple signal sources connected by cross-over switches, according to an embodiment of the present invention. A circuit 100 comprises a sequence of n signal sources 102 sources 102A, 102B, 102C, ..., 102Z, which respectively generate signals $S_1, S_2, S_3, \ldots, S_n$; n is an integer equal to or greater than two. Sources 102 have respective pairs of terminals $(S_{1a}, S_{1b}), (S_{2a}, S_{2b}), \ldots$, and the signals $S_1, S_2, S_3, \ldots, S_n$ generated across the terminals may be represented by equations similar to equations (1) and (4). Circuit 100 provides the signals it generates to a processor, herein assumed by way of example to be processor 26, via a pair of conductors 104A, 104B.

Circuit 100 also comprises a sequence of (n−1) cross-over switches 70, switches 70A, 70B, ..., 70Y. Except as described below, switches 70A, 70B and sources 102A, 102B, 102C are connected as described above for switches 70A, 70B and sources 60A, 60B, 60C (FIGS. 4A, 4B, 4C). In circuit 100 terminal $S_{1a}$ is connected to conductor 104A, but terminal T3 of switch 70B is not connected to conductor 104B.

Rather, terminal T3 of switch 70B is connected to a terminal T1 of a succeeding switch 70 (as switch 70A terminal T3 is connected to switch 70B terminal T1). The pattern of connecting terminal T3 of a given switch 70 to terminal T1 of a succeeding switch 70 continues until a final switch 70 in the sequence of switches is reached. Terminal T3 of the final, switch, illustrated as switch 70Y in the figure, is connected to conductor 104B. Thus conductor 104A is connected to a first of the n sources 102, and conductor 104B is connected to the $(n-1)^{th}$ switch 70.

For simplicity, circuit 100 has been drawn with all switches 70 in the direct configuration. In operating the circuit, processor 26 typically begins with the circuit in this configuration. The processor then toggles each of switches 70, between its direct and crossed configuration, in sequence, so that at any one time no more than one switch 70 is in the crossed configuration. When in its crossed configuration, the switch generates a "local" difference of the two signals connected to the switch. The toggling continues until the last switch in the sequence is reached. After the last switch has been toggled to its crossed configuration, it then reverts back to the direct configuration so that all switches 70 are again in the direct configuration shown in the figure. Processor 26 typically continues cycling the pattern of sequential toggling of the switches as long as signals $S_1, S_2, S_3, \ldots, S_n$ are being measured.

Outputs $V_1, V_2, V_3, \ldots, V_n$ developed across conductors 104 and received by processor 26, during the sequential toggling described above, are given by the following set of equations (11), which comprise different linear combinations of signals $S_1, S_2, S_3, \ldots, S_n$:

$$V_1 = S_1 + S_2 + S_3 + S_4 + \ldots + S_{n-1} + S_n \quad (11)$$
$$V_2 = S_1 - S_2 + S_3 + S_4 + \ldots + S_{n-1} + S_n$$
$$V_3 = S_1 + S_2 - S_3 + S_4 + \ldots + S_{n-1} + S_n$$
$$V_4 = S_1 + S_2 + S_3 - S_4 + \ldots + S_{n-1} + S_n$$
$$\ldots$$
$$V_{n-1} = S_1 + S_2 + S_3 + S_4 + \ldots - S_{n-1} + S_n$$
$$V_n = S_1 + S_2 + S_3 + S_4 + \ldots + S_{n-1} - S_n$$

From inspection of equations (11), it is apparent that the coefficient of each of the signal terms $S_1, S_2, S_3, \ldots, S_n$ in each of the equations is +1 or −1. It is also apparent that in each of the equations there is at most one "local" difference between any two terms, and that relations between all the remaining terms are sums.

Equations (11) may be written in matrix form:

$$V = M \cdot S \text{ where } V \text{ is a vector } \begin{pmatrix} V_1 \\ V_2 \\ V_3 \\ \vdots \\ V_{n-1} \\ V_n \end{pmatrix}, \quad (12)$$

$$S \text{ is a vector } \begin{pmatrix} S_1 \\ S_2 \\ S_3 \\ \vdots \\ S_{n-1} \\ S_n \end{pmatrix}, \text{ and}$$

$$M \text{ is a } n \times n \text{ matrix} \begin{bmatrix} 1 & 1 & 1 & 1 & \ldots & 1 \\ 1 & -1 & 1 & 1 & \ldots & 1 \\ 1 & 1 & -1 & 1 & \ldots & 1 \\ 1 & 1 & 1 & -1 & \ldots & 1 \\ \vdots & \vdots & \vdots & \vdots & \ddots & \vdots \\ 1 & 1 & 1 & 1 & \ldots & -1 \end{bmatrix}$$

From equation (12) an expression for signals $S_1, S_2, S_3, \ldots, S_n$, is is given by:

$$S = M^{-1} \cdot V \quad (13)$$

where $M^{-1}$ is the inverse matrix of matrix M.

Processor 26 applies equation (13), or uses an equivalent application, to derive values for signals $S_1, S_2, S_3, \ldots, S_n$ from circuit outputs $V_1, V_2, V_3, \ldots, V_n$.

Using circuits such as those described above enables processor 26 to sample multiple signals $S_1, S_2, S_3, \ldots, S_n$ substantially simultaneously, using a single pair of conductors. Thus, returning to FIG. 2, signals from coils 60A, 60B, and 60C may be sampled simultaneously via conductors 62A and 62B. Furthermore, by adding cross-over switches 70 into the distal end, other signals, such as those generated by electrodes 52, and/or those generated by sensors that may be incorporated into the distal end, such as the pressure sensor described in the above-referenced U.S. Pat. No. 8,357,152, may also be sampled via conductors 62A and 62B.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. Apparatus, comprising:
a first signal source generating a first signal and a second signal source generating a second signal;
a cross-over switch connected between the two sources so as to generate in a direct switch configuration a sum of the first and second signals and in a crossed switch configuration a difference between the first and second signals; and
a processor configured to receive the sum and the difference, and to recover the first signal and the second signal therefrom.

2. The apparatus according to claim 1, and comprising a pair of conductors, respectively connected to the first signal source and to the cross-over switch, which are configured to convey therefrom the sum and the difference to the processor.

3. The apparatus according to claim 1, wherein the first and the second signals comprise analog signals.

4. The apparatus according to claim 1, and comprising a distal end of a catheter, configured for insertion into a human patient, wherein the first signal source, the second signal source, and the cross-over switch are incorporated.

5. The apparatus according to claim 4, wherein the first and the second signal sources respectively comprise first and second coils configured to generate respectively the first signal and the second signal in response to magnetic fields generated external to the distal end, and wherein the processor is configured to determine an indication of a location and an orientation of the distal end in response to the first signal and the second signal.

6. The apparatus according to claim 1, wherein the processor is configured to toggle the cross-over switch between the direct switch configuration and the crossed switch configuration.

7. Apparatus, comprising:
a sequence of n signal sources respectively generating n signals, where n is an integer greater than one;
(n−1) cross-over switches, each cross-over switch being connected between a $p^{th}$ signal source and a $(p+1)^{th}$ signal source, where p is an integer and $1 \leq p < n$, the (n−1) cross-over switches being configured to generate n different linear combinations of the n signals; and
a processor configured to receive the linear combinations, and to recover the n signals therefrom.

8. The apparatus according to claim 7 wherein the processor is configured to cycle the (n−1) cross-over switches through n configurations of the switches so as to respectively generate the n different linear combinations of the n signals.

9. The apparatus according to claim 7, wherein respective coefficients of the n signals in the different linear combinations are +1 or −1.

10. The apparatus according to claim 7, and comprising a pair of conductors, respectively connected to a first of the n signal sources and to an $(n-1)^{th}$ cross-over switch, which are configured to convey the linear combinations to the processor.

11. A method, comprising:
generating a first signal from a first signal source and generating a second signal from a second signal source;
connecting a cross-over switch between the two sources so as to generate in a direct switch configuration a sum of the first and second signals and in a crossed switch configuration a difference between the first and second signals;
receiving the sum and the difference;
and recovering the first signal and the second signal from the sum and difference.

12. The method according to claim 11, and comprising respectively connecting a pair of conductors to the first signal source and to the cross-over switch, and conveying the sum and the difference via the pair of conductors.

13. The method according to claim 11, wherein the first and the second signals comprise analog signals.

14. The method according to claim 11, and comprising providing a distal end of a catheter configured for insertion into a human patient, and incorporating the first signal source, the second signal source, and the cross-over switch into the distal end.

15. The method according to claim 14, wherein the first and the second signal sources respectively comprise first and second coils configured to generate respectively the first signal and the second signal in response to magnetic fields generated external to the distal end, and determining an indication of a location and an orientation of the distal end in response to the first signal and the second signal.

16. The method according to claim 11, and comprising toggling the cross-over switch between the direct switch configuration and the crossed switch configuration.

17. A method, comprising:
respectively generating n signals from a sequence of n signal sources, where n is an integer greater than one;
connecting each of (n−1) cross-over switches between a $p^{th}$ signal source and a $(p+1)^{th}$ signal source, where p is an integer and $1 \leq p < n$, the (n−1) cross-over switches being configured to generate n different linear combinations of the n signals;
receiving the linear combinations; and
recovering the n signals from the received linear combinations.

18. The method according to claim 17 and comprising cycling the (n−1) cross-over switches through n configurations of the switches so as to respectively generate the n different linear combinations of the n signals.

19. The method according to claim 17, wherein respective coefficients of the n signals in the different linear combinations are +1 or −1.

20. The method according to claim 17, and comprising connecting a pair of conductors to a first of the n signal sources and to an $(n-1)^{th}$ cross-over switch, and conveying the linear combinations via the pair conductors.

* * * * *